United States Patent
Ahlmén (10) Patent No.: US 12,201,775 B2
(45) Date of Patent: Jan. 21, 2025

(54) PIERCING ASSEMBLY AND BREATHING CONDUIT KIT

(71) Applicant: MAQUET CRITICAL CARE AB, Solna (SE)

(72) Inventor: Christer Ahlmén, Sollentuna (SE)

(73) Assignee: MAQUET CRITICAL CARE AB, Solna (SE)

(*) Notice: Subject to any disclaimer, the term of this patent is extended or adjusted under 35 U.S.C. 154(b) by 791 days.

(21) Appl. No.: 16/767,095

(22) PCT Filed: Dec. 5, 2017

(86) PCT No.: PCT/SE2017/051214
§ 371 (c)(1),
(2) Date: May 26, 2020

(87) PCT Pub. No.: WO2019/112495
PCT Pub. Date: Jun. 13, 2019

(65) Prior Publication Data
US 2020/0376224 A1 Dec. 3, 2020

(51) Int. Cl.
*A61M 16/08* (2006.01)
(52) U.S. Cl.
CPC . *A61M 16/0808* (2013.01); *A61M 2202/0208* (2013.01); *A61M 2202/0225* (2013.01)
(58) Field of Classification Search
CPC ....... A61M 16/08–0808; A61M 16/0833–085; A61M 16/0875;
(Continued)

(56) References Cited

U.S. PATENT DOCUMENTS 4,284,241 A * 8/1981 Azalbert ................ B05B 1/265
239/524
5,122,122 A * 6/1992 Allgood ................ A61B 17/34
604/105
(Continued)

FOREIGN PATENT DOCUMENTS

CN 101856533 10/2010
CN 103391794 11/2013
(Continued)

OTHER PUBLICATIONS

Merriam-Webster, Definition of "bag", Downloaded on Mar. 20, 2023. (Year: 2023).*
(Continued)

*Primary Examiner* — Valerie L Woodward
(74) *Attorney, Agent, or Firm* — Fay Kaplun & Marcin, LLP (57) ABSTRACT

An assembly is configured to provide access to an interior volume of a breathing conduit. The assembly includes a piercing portion and a body portion. The piercing portion is configured to pierce through a wall of the breathing conduit to make an opening there through. The piercing portion is configured to be inserted through the opening, into the interior volume. The body portion includes a channel configured to provide fluid access to the interior volume. The assembly also includes a sealing configured to seal an area between the opening and the body portion. A breathing conduit kit includes a breathing conduit and an assembly.

18 Claims, 3 Drawing Sheets

(58) Field of Classification Search
CPC .......... A61M 16/0463–0465; A61M 16/0477; A61M 25/0084; A61M 5/178; A61M 5/32; A61M 5/347; A61M 39/10; A61B 17/00; A61B 17/34; A61B 17/3417; A61B 17/3496; A61B 2017/8675; A61B 2017/864

See application file for complete search history.

(56) References Cited

U.S. PATENT DOCUMENTS

| | | | | | |
|---|---|---|---|---|---|
| 5,330,432 | A | * | 7/1994 | Yoon | A61B 17/3417 604/164.12 |
| 5,398,677 | A | * | 3/1995 | Smith | A61M 16/0808 128/205.27 |
| 5,496,329 | A | * | 3/1996 | Reisinger | A61F 11/202 606/108 |
| 6,095,433 | A | * | 8/2000 | Langdon | A01G 27/006 222/553 |
| 2002/0017302 | A1 | * | 2/2002 | Fukunaga | A61M 16/1055 128/207.14 |
| 2004/0024371 | A1 | * | 2/2004 | Plicchi | A61M 25/0084 604/44 |
| 2004/0193100 | A1 | * | 9/2004 | Van Hooser | A61M 16/0808 604/35 |
| 2005/0267445 | A1 | * | 12/2005 | Mendels | A61M 39/10 285/120.1 |
| 2010/0137835 | A1 | * | 6/2010 | Leonhardt | A61M 25/0084 604/522 |
| 2010/0258129 | A1 | * | 10/2010 | Huschke | A61M 16/0816 128/205.27 |
| 2017/0216552 | A1 | * | 8/2017 | Goff | A61M 16/16 |
| 2019/0388641 | A1 | * | 12/2019 | Bowsher | A61M 16/0816 |

FOREIGN PATENT DOCUMENTS

| | | | |
|---|---|---|---|
| CN | 105377350 | 3/2016 | |
| CN | 107405108 | 11/2017 | |
| DE | 102013011177 A1 * | 1/2015 | ........ A61M 16/0808 |
| WO | 2008/122795 A2 | 10/2008 | |

OTHER PUBLICATIONS

Merriam-Webster, Definition of "bellows", Downloaded on Mar. 20, 2023. (Year: 2023).*
Translation of DE-102013011177-A1 (Year: 2015).*

* cited by examiner

Fig. 3

PIERCING ASSEMBLY AND BREATHING CONDUIT KIT

TECHNICAL FIELD

The present disclosure relates to an assembly configured to provide access to an interior volume of a breathing conduit by piercing through a wall of the breathing conduit. The present disclosure further relates to a breathing conduit kit.

BACKGROUND

A breathing conduit is a device for conveying gas, such as air or air/gas mixture, to and/or from the lungs of a person. Breathing conduits are used together with breathing apparatuses. Breathing apparatuses can be used to assist patients having difficulties in breathing on their own. In order to maintain oxygen saturation and carbon dioxide removal, a breathing apparatus may be used to mechanically assist or replace spontaneous breathing. Most breathing apparatuses work by increasing the patient's airway pressure through a breathing conduit connected to a patient interface, such as a mask or an endotracheal or tracheostomy tube. The increased pressure forces air to flow into the lungs. When the breathing apparatus reduces the pressure, the air is exhaled out of the patient due to the elastic properties of the lungs and the surrounding tissue. For practical reasons, breathing conduits are usually flexible but relatively not collapsible, and are usually formed by a polymeric material.

Some breathing apparatuses utilize two breathing conduits, one inspiratory conduit and one expiratory conduit. Furthermore, some breathing apparatuses utilize a coaxial breathing conduit comprising an expiratory conduit coaxially arranged around an inspiratory conduit. A problem associated with such breathing conduits is condensation of vapor due to moisture contained in the exhaled air, for example. In addition, if a humidifier is used, even the inspiratory conduit may experience vapor condensing into liquid within the conduit. As a result thereof, significant amounts of liquid may accumulate at lower portions of a breathing conduit. Liquid accumulated in a breathing conduit presents an obstruction to the flow path and decreases the ventilator performance, and may be harmful to the patient.

Moisture condensate may also be a problem in not only regulator ventilator breathing circuits, but also in closed anaesthesia breathing circuits. In these closed circuits, patient gas is recirculated via a $CO_2$ absorber and often experience excess water condensing in gas conduits.

Traditionally, the problem of condensation of vapor in breathing conduits has been handled by using water traps, or by disconnecting one end of the breathing conduit in order to drain accumulated liquid from the breathing conduit. A water trap is a device arranged at a portion of the breathing conduit and is arranged to trap liquid, such as water, accumulated in the breathing conduit. Both these methods are associated with problems. The water trap adds costs and weight to the breathing conduit and is a bulky solution. As a result thereof, disposable breathing conduits are frequently used. A disposable breathing conduit usually lacks a water trap, and is a conduit that is intended to be used once. A further problem is that when the water trap is filled with liquid, it needs to be emptied, which may cause an open connection between an interior volume of the breathing conduit and the surrounding environment. Likewise, the method where one end of the breathing conduit is disconnected inevitably causes an open connection between the interior volume of the breathing conduit and the surrounding environment.

An open connection between the interior volume of the breathing conduit and the surrounding environment causes several problems. One problem is that the pressure in the breathing conduit is reduced, which may cause the lungs of a patient to collapse, and the lungs may need to be recruited, which is a manoeuvre causing stress on lung tissue. A further problem is that when the breathing conduit is used on a breathing apparatus working with substances, such as an anaesthetic substance, the substance is released into the environment. The discharge of substances, such as an anaesthetic substance, into the surrounding environment, may be harmful for the environment, harmful for staff working in the surrounding environment, and adds cost since the discharged substance must be replaced. Further, the discharge of substances when a connection is open changes the proportion between different substances in the gas in the breathing circuit.

In addition, generally, today's consumer market requires high quality products that comprise different features and functions while the products have conditions and/or characteristics suitable for being manufactured in a cost-efficient manner.

SUMMARY OF THE DISCLOSURE

According to a first aspect of the present disclosure, the object is achieved by an assembly configured to provide access to an interior volume of a breathing conduit. The assembly comprises a piercing portion and a body portion, wherein the piercing portion is configured to pierce through a wall of the breathing conduit to make an opening there through. The piercing portion is configured to be inserted through the opening, into the interior volume, in a first direction. The body portion is configured to extend through the opening when the piercing portion is inserted into the interior volume. The body portion comprises a channel configured to provide fluid access to the interior volume. The assembly further comprises a sealing configured to seal an area between the opening and the body portion.

As a result, an assembly is provided allowing a user to obtain access to an interior volume of a breathing conduit, when needed, in a quick, safe and simple manner.

Since the assembly comprises a sealing configured to seal the area between the opening and the body portion, the risk of leakage through the area is significantly reduced, and fluid may be evacuated from, or added to, the interior volume of the breathing conduit in a simple and controlled manner, without significantly reducing the pressure in the interior volume of the breathing conduit.

That is, in case liquid is accumulated in a portion of the breathing conduit, a user may simply grab the body portion of the assembly and pierce the piercing portion through a wall of the conduit at the portion and insert the piercing portion into the interior volume. As a result, the liquid will flow out from the interior volume via the channel. Accordingly, an assembly is provided allowing a user to evacuate accumulated liquid from a breathing conduit in a quick, safe and simple manner.

Further, in case a user wants to obtain quick access to the interior volume of the breathing conduit in order to add a substance to the interior volume, the user may simply grab the body portion of the assembly and pierce the piercing portion through a wall of the conduit at the portion and insert the piercing portion into the interior volume. Then, the user may simply add the substance via the channel, in a quick, safe and simple manner.

Thus, an assembly is provided allowing a user to obtain access to an interior volume of a breathing conduit with a reduced risk of an uncontrolled reduction in pressure in the breathing conduit and with a reduced risk of discharge of substances, such as anaesthetic substances, into the environment. Further, since a simple assembly is provided comprising few components, it can be manufactured in a cost-efficient manner.

Accordingly, an assembly is provided overcoming, or at least alleviating, at least some of the above-mentioned problems and drawbacks. As a result, the above-mentioned object is achieved.

Optionally, the sealing comprises an elastic material. Thereby, the sealing capability of the sealing is improved which further reduces the risk of leakage through the opening and the body portion.

Optionally, the sealing is arranged around the body portion. Thereby, the sealing capability of the sealing is further improved which further reduces the risk of leakage through the opening and the body portion. In addition, the sealing can be provided in a cost-efficient manner, for example by providing the sealing in a tubular shape around the body portion.

Optionally, the channel extends through the body portion and the piercing portion. Thereby, access to the interior volume is ensured, when the piercing portion is inserted into the interior volume, in a simple and efficient manner.

Optionally, the piercing portion comprises an abutment surface configured to abut against an inner wall surface of the breathing conduit. Thereby, the risk of an unintended displacement of the piercing portion out of the interior volume is reduced. As a result, a controlled access to the interior volume is further ensured, the risk of discharge of substances into the environment is further reduced, and the risk of an unintended reduction of pressure in the breathing conduit is further reduced.

Optionally, the abutment surface comprises a surface normal pointing in a second direction, wherein the second direction is substantially opposite to the first direction. Thereby, the risk of an unintended displacement of the piercing portion out of the interior volume is further reduced, which further ensures a controlled access to the interior volume, further reduces the risk of discharge of substances into the environment, and further reduces the risk of an unintended reduction of pressure in the breathing conduit.

Optionally, the abutment surface is annular. Thereby, the risk of an unintended displacement of the piercing portion out of the interior volume is further reduced, which further ensures a controlled access to the interior volume, further reduces the risk of discharge of substances into the environment, and further reduces the risk of an unintended reduction of pressure in the breathing conduit.

Optionally, the piercing portion is conical. Thereby, the piercing portion is able to pierce through a wall of the breathing conduit to make an opening there through in a simple and controlled manner. Further, the piercing portion can be inserted through the opening, in a simple and controlled manner.

Optionally, the abutment surface is a surface of the widest portion of the piercing portion measured in a direction perpendicular to the first direction. Thereby, the risk of an unintended displacement of the piercing portion out of the interior volume is further reduced, which further ensures a controlled access to the interior volume, further reduces the risk of discharge of substances into the environment, and further reduces the risk of an unintended reduction of pressure in the breathing conduit. In addition, since the abutment surface is a surface of the widest portion of the piercing portion measured in a direction perpendicular to the first direction, the piercing portion is able to pierce through a wall of the breathing conduit in a simple and controlled manner. Further, the piercing portion can be inserted through the opening, in a simple and controlled manner.

Optionally, the piercing portion comprises at least one thread extending along more than 50% of the piercing portion in the first direction. Thereby, the piercing through the wall is further facilitated.

Optionally, the assembly comprises a valve arranged to allow control of flow of fluid through the channel. Thereby, an assembly is provided allowing a user to obtain access to an interior volume of a breathing conduit in a still more controlled manner.

That is, when using the assembly, a user may check that the valve is closed and may simply grab the body portion of the assembly and pierce the piercing portion through a wall of the conduit and insert the piercing portion into the interior volume. Then, the user may open the valve to obtain access to the interior volume, for example, in order to evacuate accumulated liquid from the interior volume, or in order to add a substance into the interior volume. Then, the user may close the valve to hinder further fluid transport through the channel. Thus, due to the valve, and due to the sealing that seals the area between the opening and the body portion, the assembly may remain inserted into the breathing conduit after use. Further, the assembly can be used later to evacuate accumulated liquid from the interior volume, or to add a substance to the interior volume, simply by opening the valve.

Optionally, the assembly is configured to provide access to interior volumes of a coaxial breathing conduit comprising a first conduit and a second conduit, wherein the second conduit is coaxially arranged around the first conduit, wherein the piercing portion is configured to pierce through a second wall of the second conduit to make a second opening there through, and through a first wall of the first conduit to make a first opening there through, wherein the piercing portion is configured to be inserted through the openings, into a first interior volume of the first conduit, wherein the body portion is configured to extend through the openings, when the piercing portion is inserted into the first interior volume, wherein the sealing is configured to seal an area between the first opening and the body portion, and wherein the body portion comprises a first channel configured to provide access to the first interior volume, and a second channel configured to provide access to the second interior volume.

As a result, an assembly is provided allowing a user to obtain access to interior volumes of a coaxial breathing conduit comprising a first and a second conduit, when needed, in a quick, safe and simple manner.

Further, an assembly is provided allowing a user to obtain access to interior volumes of a coaxial breathing conduit with a reduced risk of an uncontrolled reduction in pressure in the conduits and with a reduced risk of discharge of substances, such as anaesthetic substances, into the environment.

Optionally, the assembly further comprises a second sealing configured to seal an area between the second opening and the body portion. Thereby, the risk of leakage through the area between the second opening and the body portion is significantly reduced, which reduces the risk of an uncontrolled reduction in pressure in the second conduit and reduces the risk of discharge of substances, such as anaesthetic substances, from the second conduit into the environment.

Optionally, the body portion comprises a second abutment surface configured to abut against an inner wall surface of the second conduit. Thereby, the risk of an unintended displacement of the assembly out of the breathing conduit is further reduced. As a result, a controlled access to the interior volumes is further ensured, the risk of discharge of substances into the environment is further reduced, and the risk of an unintended reduction of pressure in the conduits is further reduced.

Optionally, the assembly comprises a first valve arranged to allow control of flow of fluid through the first channel, and a second valve arranged to allow control of flow of fluid through the second channel. Thereby, an assembly is provided allowing a user to obtain access to interior volumes of a coaxial breathing conduit in a still more controlled manner.

That is, when using the assembly, a user may check that the first and second valves are closed and may simply grab the body portion of the assembly and pierce the piercing portion through the walls of the conduit and insert the piercing portion into the first interior volume. Then, the user may open the first valve to obtain access to the first interior volume, or may open the second valve to obtain access to the second interior volume, for example, in order to evacuate accumulated liquid from an interior volume, or in order to add a substance into an interior volume. Then, the user may close the valve to hinder further fluid transport through the channel. Thus, due to the valves, the assembly may remain inserted into the breathing conduit after use. Further, the assembly can be used later to evacuate accumulated liquid from the interior volumes, or to add a substance to the interior volumes, in a controlled manner, simply by using the valves.

Further, since the assembly comprises the first and second valves, fluid transport between the first and second inner volumes, via the first and second channels, can be avoided simply by ensuring that only one of the first and second valve is open at a time.

Optionally, the assembly comprises an access port arranged at an end of the channel. Thereby, evacuation of accumulated liquid from an interior volume is facilitated, and insertion of a substance to an interior volume is facilitated, for example, by using a second device, such as a syringe, inserted into the access port.

Optionally, the assembly comprises a fluid reservoir connected to the channel, and wherein at least a portion of the fluid reservoir is flexible. Thereby, accumulated liquid can be evacuated from an interior volume in a simple and efficient manner, for example, by being pumped out by pressure variations in the breathing conduit. Further, the risk of a discharge of a substance into the environment is further reduced, and the risk of an unintended reduction of pressure in the conduits is further reduced.

Optionally, the fluid reservoir is a flexible bag. Thereby, a simple and efficient fluid reservoir is provided, which can be manufactured in a cost-efficient manner.

Optionally, the fluid reservoir comprises a bellow. Thereby, a simple and efficient fluid reservoir is provided, which further facilitates evacuation of accumulated liquid from an interior volume of the breathing conduit. For example, the bellow can ensure that liquid is pumped out by pressure variations in the breathing conduit, and/or can be used to perform a manual evacuation of the liquid from the interior volume of the breathing conduit.

According to a second aspect of this disclosure, the object is achieved by a breathing conduit kit comprising a breathing conduit and an assembly according to embodiments described above, wherein the assembly is configured to provide access to an interior volume, of the breathing conduit.

As a result, a breathing conduit kit is provided allowing a user to obtain access to an interior volume of the breathing conduit, when needed, in a quick, safe and simple manner.

Thus, a breathing conduit kit is provided allowing a user to obtain access to an interior volume of a breathing conduit with a reduced risk of an uncontrolled reduction in pressure in the breathing conduit and with a reduced risk of discharge of substances, such as anaesthetic substances, into the environment. Further, since a simple breathing conduit kit is provided, that comprises few components, the breathing conduit kit can be manufactured in a cost-efficient manner.

Accordingly, a breathing conduit kit is provided overcoming, or at least alleviating, at least some of the above-mentioned problems and drawbacks. As a result, the above-mentioned object is achieved.

Further features of, and advantages with, the present invention will become apparent when studying the appended claims and the following detailed description.

BRIEF DESCRIPTION OF THE DRAWINGS

Various aspects of the invention, including its particular features and advantages, will be readily understood from the non-limiting example embodiments discussed in the following detailed description and the accompanying drawings, in which.

DETAILED DESCRIPTION

Aspects of the present invention will now be described more fully. Like numbers refer to like elements throughout. Well-known functions or constructions will not necessarily be described in detail for brevity and/or clarity.

Figure 1:
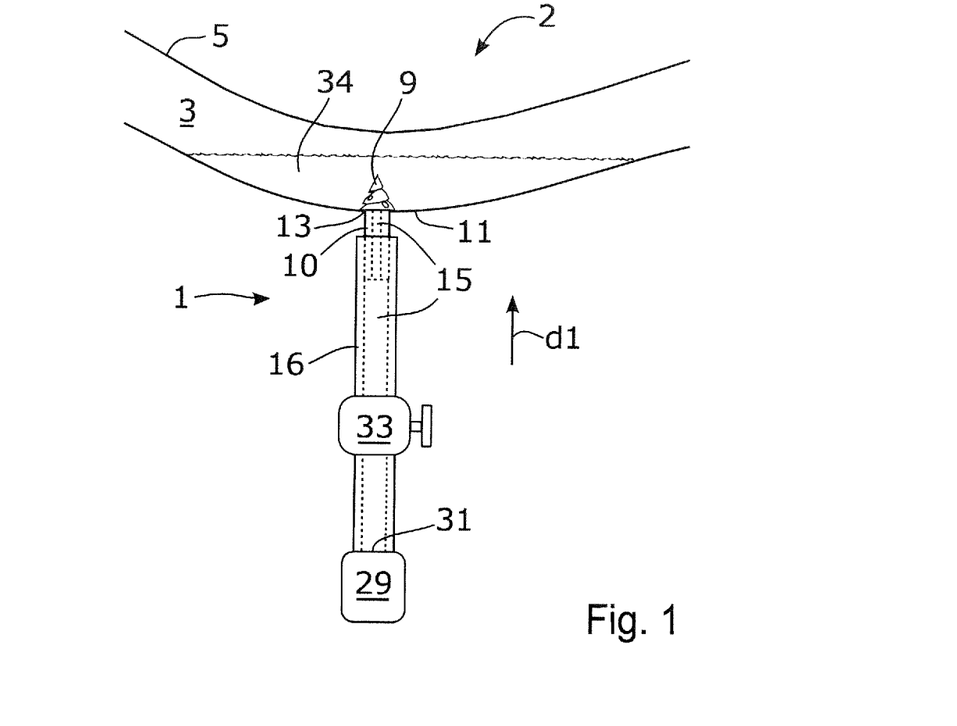
FIG. 1 illustrates an assembly configured to provide access to an interior volume of a breathing conduit.

FIG. 1 illustrates a breathing conduit kit 2 comprising a breathing conduit 5 and an assembly 1 configured to provide access to an interior volume 3 of the breathing conduit 5. The breathing conduit 5 is flexible and is formed by a polymeric material. For example, the breathing conduit 5 may be formed by medical grade polyethylene, polypropylene (PP), and/or polyvinyl chloride (PVC). The assembly 1 comprises a body portion 10, and a piercing portion 9 arranged at an end of the body portion 10. The piercing portion 9 is configured to pierce through a wall 11 of the breathing conduit 5 to make an opening 13 through the wall 11. The piercing portion 9 is configured to be inserted through the opening 13, into the interior volume 3, in a first direction d1. As illustrated, the body portion 10 is configured to extend through the opening 13 when the piercing portion 9 is inserted into the interior volume 3. Further, the body portion 10 comprises a channel 15 configured to provide fluid access to the interior volume 3.

Figure 2:
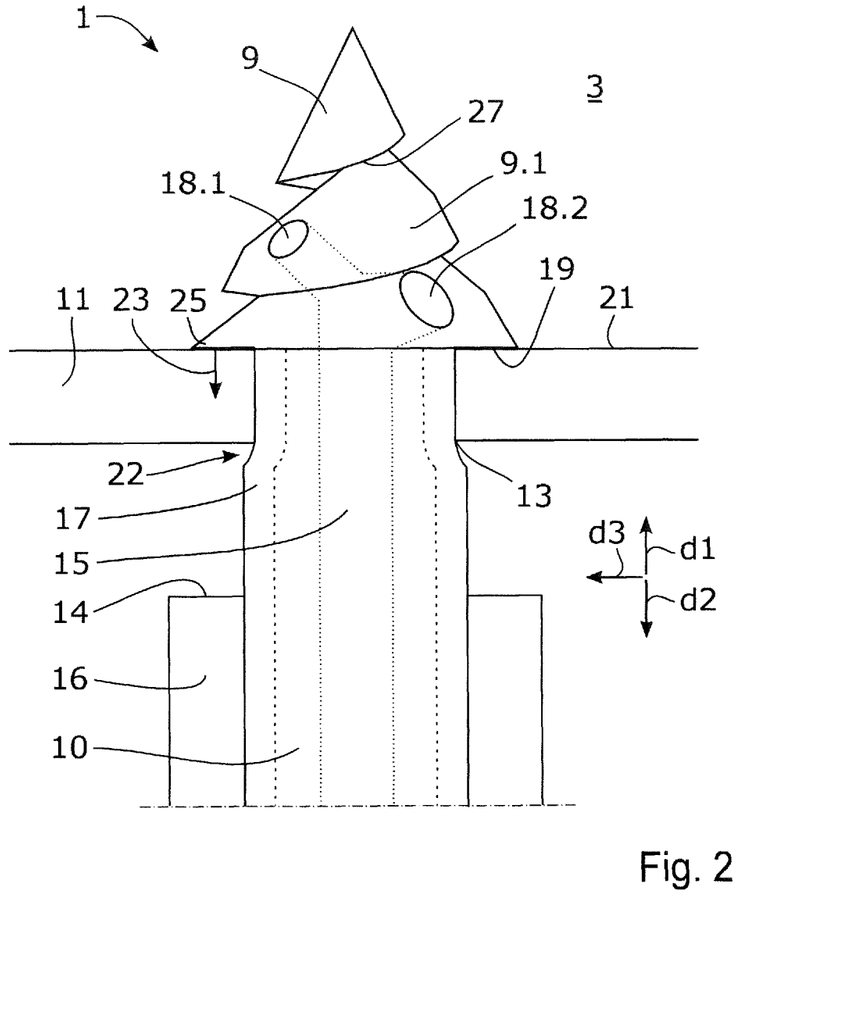
FIG. 2 illustrates an enlarged view of the assembly, according to the embodiments illustrated in FIG. 1, and FIG. 3 schematically illustrates an assembly, according to some further embodiments.

FIG. 2 illustrates an enlarged view of the assembly 1, according to the embodiments illustrated in FIG. 1. The piercing portion 9 of the assembly 1 is inserted through an opening 13 in a wall 11 of the breathing conduit into the interior volume 3 of the breathing conduit. The assembly 1 comprises a sealing 17 configured to seal an area between the opening 13 and the body portion 10. The area between the opening 13 and the body portion 10 may be sealed as a result of a compression fit formed between the sealing 17 and the material of the wall 11 that springs back against the sealing 17 after the opening 13 is formed by manually forcing the piecing portion 9 through the wall 11.

According to the illustrated embodiments, the sealing 17 is arranged around the body portion 10 and extends along a great proportion of the body portion 10 seen in the first direction d1. Thereby, the sealing 17 is capable of sealing the area between the opening 13 and the body portion 10 at different relative positions between the assembly 1 and the wall 11 of the breathing conduit, in the first direction d1. That is, since the sealing 17 extends along a great proportion of the body portion 10 seen in the first direction d1, the sealing 17 will seal the area between the opening 13 and the body portion 10 even if the assembly 1 is displaced a distance in the first direction d1 relative the wall 11.

According to the illustrated embodiments, the assembly 1 comprises a stop surface 14 configured to abut against the wall 11 if the assembly 1 is displaced a certain distance in the first direction d1 relative the wall 11. According to the illustrated embodiments, the stop surface 14 is a surface of a tube 16 coaxially arranged around the body portion 10. The tube 16 is also indicated in FIG. 1. According to further embodiments, the stop surface 14 may be a surface of another type of component extending in a radial direction of the body portion 10. Such a component may be a non-annular component, or may be an annular component, so as to form an annular stop surface 14. According to the embodiments illustrated in FIG. 1, the body portion 10 is formed by a single tubular piece of a polymeric material, such as medical grade polyethylene, polypropylene (PP), and/or polyvinyl chloride (PVC). Further, the sealing 17 is formed by a single tubular piece of material arranged around the body portion 10. The sealing 17 may comprise an elastic material, such as silicone. The piercing portion 9 is attached to an end of the body portion 10 and may also be formed by a polymeric material, such as medical grade polyethylene, polypropylene (PP), and/or polyvinyl chloride (PVC). The piercing portion 9 may be provided such that the piercing portion 9 is harder than the wall 11 of the breathing conduit. A second end of the body portion 10 is inserted in an elastic tube 16 having an inner diameter slightly smaller than an outer diameter of the body portion 10. Due to these features, the assembly 1 can be manufactured in a simple and cost-effective manner.

When the piercing portion 9 is piercing through the wall 11 of the breathing conduit 5, the material of the breathing conduit 5 around the opening 13 is expanding. When the piercing portion 9 is inserted through the opening 13 into the interior volume 3, the material of the breathing conduit around the opening 13 may be compressed, i.e. may spring back around the sealing 17, which may result in a slightly compressed sealing 17. In this manner, a gas tight seal of the area between the opening 13 and the body portion 10 can be further ensured.

According to the illustrated embodiments, the channel 15 extends through the body portion 10 and the piercing portion 9. The channel 15 comprises three openings in a surface 9.1 of the piercing portion 9. In FIG. 2, only two openings 18.1, 18.2 are visible because the third opening is on the rear side of the piercing portion 9. The channel 15 may comprise another number of openings 18.1, 18.2 than three, for example, one, two, four, five, or six. In embodiments where the channel 15 comprises more than one opening, fluid transport into, and out of, the channel 15 is ensured while the openings 18.1, 18.2 have a low impact on the ability of the piercing portion 9 to pierce through the wall 11 of the breathing conduit, and on the ability of the piercing portion 9 to be inserted through the opening 13.

Further, according to the illustrated embodiments, the piercing portion 9 is conical. That is, according to the illustrated embodiments, the surface 9.1 of the piercing portion that comprises the openings 18.1, 18.2 is a conical surface 9.1. The piercing portion 9 comprises at least one thread 27 extending along substantially the entire conical surface 9.1 in the first direction d1. According to further embodiments, the thread 27 may extend along more than 50%, 60%, 70%, 80%, or 90% of the conical surface 9.1 in the first direction d1. Due to these features, the process of piercing the piercing portion 9 through the wall is facilitated, as well as the process of inserting the piercing portion 9 through the opening 13.

Further, according to the illustrated embodiments, the piercing portion 9 comprises an abutment surface 19 configured to abut against an inner wall surface 21 of the breathing conduit 5 when the assembly 1 is displaced in a second direction d2, being opposite to the first direction d1. The abutment surface 19 is an annular surface of the widest portion 25 of the piercing portion 9 measured in a direction d3 perpendicular to the first direction d1, i.e., a direction d3 perpendicular to the insertion direction d1 of the piercing portion 19. The abutment surface 19 comprises a surface normal 23 pointing in the second direction d2. The second direction d2 may be substantially opposite to the first direction d1, within the meaning that an angle between the first and second directions d1, d2 is more than 160 degrees. Due to these features, the risk is significantly reduced of an unintended displacement of the piercing portion 9 out of the opening 13, in the second direction d2.

Thus, according to the illustrated embodiments, the abutment surface 19 hinders displacement of the assembly 1 in the second direction d2, and the stop surface 14 hinders displacement of the assembly 1 in the first direction d1. According to the illustrated embodiments, the sealing 17 covers the entire extension of the body portion 10 between the stop surface 14 and the abutment surface 19. As a result, the sealing 17 will seal the area between the opening 13 and the body portion 10 when the abutment surface 19 is abutting against the inner wall surface 21 of the breathing conduit, as is illustrated in FIG. 2, and when the assembly 1 is in a position where the stop surface 14 is abutting against the wall 11 of the breathing conduit, as well as when the assembly 1 is in any position between these positions.

As an alternative to, or in addition to, the sealing 17 illustrated in FIG. 1, the assembly 1 may comprise a sealing at the abutment surface 19 configured to seal the area between the opening 13 and the body portion 10. Further, according to some embodiments, the sealing 17 may comprise a groove 22 in the body portion 10 between the abutment surface 19 and the stop surface 14, wherein the groove 22 is configured to seal the area between the opening 13 and the body portion 10.

According to the embodiments illustrated in FIG. 1, the assembly 1 comprises a valve 33 arranged to allow control of flow of fluid through the channel 15. Further, the assembly 1 comprises an access port 29 arranged at an end 31 of the channel 15. The channel 15 extends from the openings 18.1, 18.2 in the piercing portion 9, indicated in FIG. 2, to the access port 29, illustrated in FIG. 1. The access port 29 facilitates evacuation of accumulated liquid 34 from the interior volume 3, and facilitates the insertion of a substance to the interior volume 3. That is, a user may check that the valve 33 is closed and may simply grab the body portion 10 of the assembly 1, or grab the tube 16 of the assembly 1, and pierce the piercing portion 9 through the wall 11 of the breathing conduit 5 to insert the piercing portion 9 into the interior volume 3. Then, the user may insert a second device, such as a syringe, into the access port 29 and open the valve 33 to open a connection between the inner volume 3 and the access port 29. The access port 29 as referred to herein may also be referred to as a fluid port 29, or a mouthpiece 29. Then, the user may evacuate accumulated liquid 34 from the interior volume 3, or add a substance to the interior volume 3, using the second device. The positive pressure in the breathing conduit may ensure that accumulated liquid 34 is evacuated from the interior volume 3 via the access port 29. Then the user may close the valve 33 to hinder further fluid transport through the channel 15.

Since the assembly 1 comprises the valve 33 and since the sealing 17 seals the area between the opening 13 and the body portion 10, the assembly 10 may remain inserted into the breathing conduit 5 after use of the assembly 1, and the user may, at a later stage, obtain repeated fluid access to the interior volume 3 simply by opening the valve 33 in order to remove fluid or add fluid via the access port 29.

Figure 3:
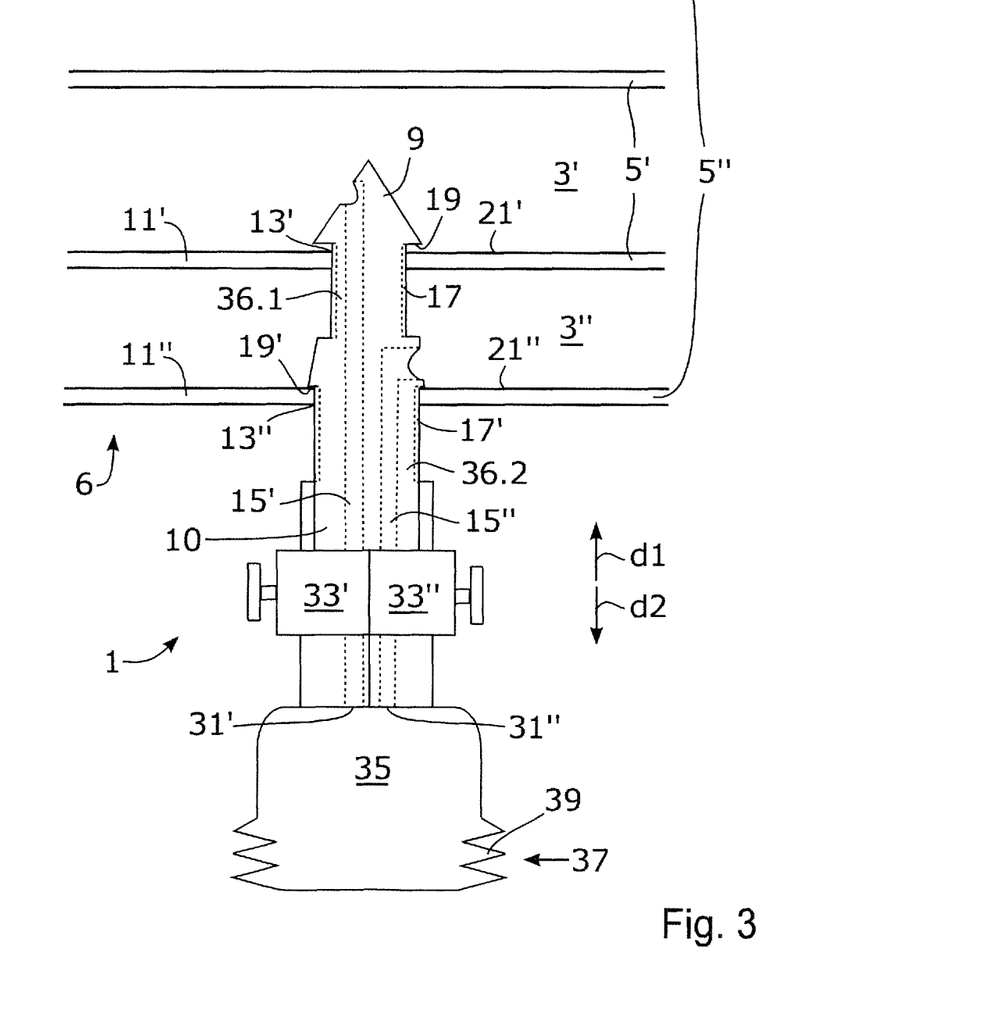

FIG. 3 schematically illustrates an assembly 1, according to some further embodiments. The assembly 1 is configured to provide access to first and second interior volumes 3', 3" of a coaxial breathing conduit 6 comprising a first conduit 5' and a second conduit 5". The second conduit 5" is coaxially arranged around the first conduit 5'. The first and second conduits 5', 5" are flexible and are formed by a polymeric material, such as medical grade polyethylene, polypropylene (PP), and/or polyvinyl chloride (PVC). The first conduit 5' may be an inspiratory conduit and the second conduit 5" may be an expiratory conduit. The piercing portion 9 is configured to pierce through a second wall 11" of the second conduit 5" to make a second opening 13" there through, and through a first wall 11' of the first conduit 5' to make a first opening 13' there through. The piercing portion 9 is configured to be inserted through the first and second openings 13', 13", in a first direction d1, into a first interior volume 3' of the first conduit 5'. The body portion 10 is configured to extend through the first and second openings 13', 13" when the piercing portion 9 is inserted into the first interior volume 3'. A sealing 17 is configured to seal an area between the first opening 13' and the body portion 10. The body portion 10 comprises a first channel 15' configured to provide access to the first interior volume 3', and a second channel 15" configured to provide access to the second interior volume 3". Thus, by inserting the piercing portion 9 into the first interior volume 3', access is provided to the first interior volume 3', as well as to the second interior volume 3" because the first channel 15' extends farther than the second channel 15" and the first channel 15' is contiguous with at least one or more openings in the piercing portion 9, whereas the second channel 15" is contiguous with at least one or more openings formed in a portion of the body portion 10.

According to the illustrated embodiments, the assembly 1 comprises a second sealing 17' configured to seal an area between the second opening 13" and the body portion 10. The piercing portion 9 comprises an abutment surface 19 configured to abut against an inner wall surface 21' of the first conduit 5' of the breathing conduit 6 when the assembly 1 is displaced in a second direction d2, being opposite to the first direction d1. Further, according to the illustrated embodiments, the body portion 10 comprises a second abutment surface 19' configured to abut against an inner wall surface 21" of the second conduit 5" of the breathing conduit 6. The second abutment surface 19' is provided by the abutment portion of the body portion 10. Due to these features, the risk of an unintended displacement of the piercing portion 9 out of the first opening 13', in a second direction d2, is significantly reduced.

According to the illustrated embodiments, the sealing 17 is arranged around a first portion 36.1 of the body portion 10, i.e. a portion of the body portion 10, below the piercing portion 9, seen in the first direction d1. The second sealing 17' is arranged around a second portion 36.2 of the body portion 10, i.e. a portion of the body portion 10 below the second abutment surface 19', seen in the first direction d1. The sealing 17 and the second sealing 17' each extends along a substantial proportion of the body portion 10 seen in the first direction d1. As a result, the sealing 17 will seal the area between the first opening 13' and the body portion 10, and the second sealing 17' will seal the area between the second opening 13" and the body portion 10, even if the assembly 1 is displaced a distance in the first direction d1 relative the walls 11', 11". The sealing 17 and the second sealing 17' may each comprise an elastic material, such as silicone, and may each be formed as a tube arranged around a portion 36.1, 36.2 of the body portion 10. The abutment portion is disposed between the sealing 17 and the second sealing 17' as evident from FIG. 3.

As an alternative to, or in addition to, the sealing 17 and the second sealing 17' illustrated in FIG. 3, the assembly 1 may comprise a sealing at the abutment surface 19 configured to seal the area between the first opening 13' and the body portion 10, and/or a sealing at the second abutment surface 19' configured to seal the area between the second opening 13" and the body portion 10.

According to the illustrated embodiments, an outer diameter of the first portion 36.1 is smaller than an outer diameter of the second portion 36.2. Furthermore, an outer diameter of the first sealing 17 is smaller than an outer diameter of the second sealing 17'. As a result thereof, the diameter of the first opening 13' is smaller than the diameter of the second opening 13". Due to these features, the piercing through the walls 11", 11' is facilitated and a tight seal of the area between the body portion 10 and the second opening 13" is ensured.

The assembly comprises a first valve 33' arranged to allow control of flow of fluid through the first channel 15', and a second valve 33" arranged to allow control of flow of fluid through the second channel 15". Further, the assembly 1 may comprise a fluid reservoir 35 connected to the first and second channels 15', 15". At least a portion 37 of the fluid reservoir 35 is flexible which facilitates transport of fluid into the fluid reservoir 35.

In order to evacuate accumulated liquid in the first conduit 5', a user may simply open the first valve 33' while the second valve 33" is closed. As a result thereof, the liquid will flow from the first interior volume 3' to the fluid reservoir 35, via the first channel 15'. Then, the user may close the first valve 33' to hinder further fluid transport through the first channel 15'. In order to evacuate accumulated liquid in the second conduit 5", a user may simply open the second valve 33". As a result thereof, the liquid will flow from the second interior volume 3" to the fluid reservoir 35, via the second channel 15". Then, the user may close the second valve 33" to hinder further fluid transport through the second channel 15".

Due to the first and second valves 33', 33" and due to the sealing 17 and the second sealing 17', the assembly 1 may remain inserted into the breathing conduit 5 after use of the assembly 1, and the user may, at a later stage, obtain selectable access to the first interior volume 3' simply by opening the first valve 33' while the second valve 33" is closed, and obtain selectable access to the second interior volume 3" simply by opening the second valve 33", while the first valve 33' is closed. Further, since the assembly 1 comprises the first and second valves 33', 33", fluid transport between the first and second inner volumes 3', 3", via the first and second channels 15', 15" and the fluid reservoir 35, can be avoided simply by ensuring that only one of the first and second valve 33', 33" is open at a time.

According to the illustrated embodiments, the fluid reservoir 35 comprises a bellow 39. Since fluid reservoir 35 comprises a flexible portion 37, such as the bellow 39, pressure variations in the breathing conduits 5', 5" may pump accumulated liquid from the inner volumes 3', 3" through the channels 15', 15". According to further embodiments, the fluid reservoir may comprise a flexible bag, or the like. Further, the assembly 1 according to the embodiments illustrated in FIG. 3, may comprise an access port 29, as illustrated in FIG. 1, instead of the fluid reservoir 35. According to such embodiments, such an access port 29 may be arranged at a respective end 31', 31" of the first and second channel 15', 15", respectively. Of course, instead of a single access port 29 connected to both channels 15', 15", each channel 15', 15" may be provided with its own separate access port.

Further, the assembly 1, according to the embodiments illustrated in FIG. 1 and FIG. 2, may comprise fluid reservoir 35 as described in accordance with the embodiments illustrated in FIG. 3, instead of the access port 29. Further, the assembly 1, according to the embodiments illustrated in FIG. 3, may comprise a piercing portion 9 as described with reference to FIG. 1 and FIG. 2.

The valve 33, the first valve 33' and/or the second valve 33" may comprise a valve 33, 33', 33" configured to automatically open when a fluid reservoir 35 is connected thereto, and automatically close when a fluid reservoir is disconnected therefrom. Further, the valve 33, the first valve 33' and/or the second valve 33" may comprise a valve 33, 33', 33" arranged in an access port 29, as referred to herein, wherein the valve 33, 33', 33" is configured to automatically open when a second device, such as a syringe, is inserted into the access port 29, and automatically close when the second device is removed from the access port 29.

According to some embodiments, the body portion 10, as referred to herein, may be formed by a sealing material, such as an elastic material. According to such embodiments, the body portion 10 may be formed by an elastic material, wherein the body portion 10 is provided such that the elasticity of the material increases along a radial direction of the body portion 10. Thus, according to such embodiments, as well as according to other embodiments described herein, the body portion 10 and the sealing 17 may be comprised in the same part.

It is to be understood that the foregoing is illustrative of various example embodiments and that the invention is defined only by the appended claims. A person skilled in the art will realize that the example embodiments may be modified, and that different features of the example embodiments may be combined to create embodiments other than those described herein, without departing from the scope of the present invention, as defined by the appended claims.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. An assembly configured to provide access to an interior volume of a breathing conduit, comprising:
a body portion including a first channel extending therethrough;
a piercing portion extending from a first end and tapering toward a second end, the first end attached to at an end of the body portion, wherein the piercing portion is configured to pierce through a wall of the breathing conduit to make an opening therethrough such that the piercing portion is configured to be inserted through the opening, into the interior volume, in a first direction, the first end of the piercing portion including defining an abutment surface at an end thereof so that, when the piercing portion is inserted into the interior volume, the abutment surface is configured to abut an inner wall of the breathing conduit and the body portion extends from the piercing portion, in a second direction opposite the first direction, to extend through the opening so that the first channel provides fluid access to the interior volume; and
a sealing extending along a portion of the body portion and configured to be received within the opening, the sealing formed of an elastic material configured to seal an area between the opening and the body portion via a compression fit.

2. The assembly according to claim 1, wherein the sealing is arranged around the body portion.

3. The assembly according to claim 1, wherein the first channel extends through both the body portion and the piercing portion.

4. The assembly according to claim 1, wherein the abutment surface comprises a surface normal pointing in the second direction and wherein the second direction is substantially opposite of the first direction.

5. The assembly according to claim 1, wherein the abutment surface is annular.

6. The assembly according to claim 1, wherein the piercing portion is conical.

7. The assembly according to claim 1, wherein the abutment surface is a surface of the widest portion of the piercing portion measured in a direction perpendicular to the first direction.

8. The assembly according to claim 1, wherein the piercing portion comprises at least one thread extending along more than 50% of the piercing portion in the first direction.

9. The assembly according to claim 1, further comprising:
a valve arranged to allow control of flow of fluid through the first channel.

10. The assembly according to claim 1,
wherein the assembly is configured to provide access to interior volumes of a coaxial breathing conduit comprising a first conduit and a second conduit,
wherein the second conduit is coaxially arranged around the first conduit, wherein the piercing portion is configured to pierce through a second wall of the second conduit to make a second opening there through, and through a first wall of the first conduit to make a first opening therethrough,
wherein the piercing portion is configured to be inserted through the first and second openings, into a first interior volume of the first conduit, wherein the body portion is configured to extend through the first and second openings when the piercing portion is inserted into the first interior volume, wherein the sealing is configured to seal an area between the first opening and the body portion, and wherein the body portion further comprises a second channel so that the first channel is configured to provide access to the first interior volume while the second channel is configured to provide access to a second interior volume of the second conduit.

11. The assembly according to claim 10, further comprising:
a second sealing configured to seal an area between the second opening and the body portion.

12. The assembly according to claim 10, wherein the body portion comprises a second abutment surface configured to abut against an inner wall surface of the second conduit.

13. The assembly according to claim 10, further comprising:
a first valve arranged to allow control of flow of fluid through the first channel; and
a second valve arranged to allow control of flow of fluid through the second channel.

14. The assembly according to claim 1, further comprising:
an access port arranged at an end of the first channel.

15. The assembly according to claim 1, further comprising:
a fluid reservoir connected to the first channel,
wherein at least a portion of the fluid reservoir is flexible.

16. The assembly according to claim 15, wherein the fluid reservoir is a flexible bag.

17. The assembly according to claim 15, wherein the fluid reservoir comprises a bellow.

18. A breathing conduit kit, comprising:
a breathing conduit; and
the assembly according to claim 1,
wherein the assembly is configured to provide access to an interior volume of the breathing conduit.

* * * * *